United States Patent
Bejerano et al.

(10) Patent No.: US 6,241,864 B1
(45) Date of Patent: Jun. 5, 2001

(54) ON-LINE ANALYZER FOR ACTIVE HALOGENS

(75) Inventors: Tuvia Tony Bejerano, Omer; Chaim N. Yarnitsky, Haifa; Miriam Freiberg Bergstein, Omer, all of (IL)

(73) Assignee: Bromine Compounds Ltd. (IL)

( * ) Notice: Subject to any disclaimer, the term of this patent is extended or adjusted under 35 U.S.C. 154(b) by 0 days.

(21) Appl. No.: 09/407,812

(22) Filed: Sep. 28, 1999

Related U.S. Application Data

(63) Continuation of application No. PCT/IL98/00136, filed on Mar. 26, 1998.

(30) Foreign Application Priority Data

Apr. 6, 1997 (IL) .................................................. 120615

(51) Int. Cl.[7] .................................................. G02N 27/26
(52) U.S. Cl. .................................................. 204/411; 204/409
(58) Field of Search .................................................. 204/409, 411, 204/412, 416, 406; 205/778.5

(56) References Cited

U.S. PATENT DOCUMENTS

| | | | |
|---|---|---|---|
| 3,461,043 | * 8/1969 | Guerrant | 205/779.5 |
| 4,033,830 | 7/1977 | Fletcher, III | 204/1 T |
| 4,040,931 | * 8/1977 | Wilson | 204/404 |
| 4,726,929 | 2/1988 | Gropper et al. | 422/68 |

FOREIGN PATENT DOCUMENTS

| | | |
|---|---|---|
| 0 016 414 | 3/1980 | (EP) . |
| 0 020 898 | 4/1980 | (EP) . |
| 0 068 101 | 4/1982 | (EP) . |
| 0 471 986 A2 | 7/1991 | (EP) . |
| 0 471 986 A3 | 7/1991 | (EP) . |
| 2 062 698 | 6/1971 | (FR) . |
| 2 675 260 | 10/1992 | (FR) . |

OTHER PUBLICATIONS

Derwent abstract Chopin et al. (FR 2675260A1).*
Bard et al., "Electrochemical Methods—Fundamentals and Applications," John Wiley & Sons, 1980, p. 563.
Patents Abstracts of Japan JP–57042845 (Yokogawa Hokoshia Electric Corp) Inventor: Muramoto Setsuo.
Abstract Chopin et al. (FR2675260).

* cited by examiner

Primary Examiner—T. Tung
Assistant Examiner—Alex Noguerola
(74) Attorney, Agent, or Firm—Lerner, David, Littenberg, Krumholz & Mentlik, LLP

(57) ABSTRACT

A potentiostatic analyzer for active halogens in conducting solutions that contain also the corresponding halide comprises, in combination: a) a concentration-to-current transducer, which is an electrolytic cell; b) means for providing a controlled flow of the solution being analyzed through the cell; and c) a potentiostatic transmitter for controlling the electrodes of the electrolytic cell.

9 Claims, 3 Drawing Sheets

ON-LINE ANALYZER FOR ACTIVE HALOGENS

CROSS-REFERENCE TO RELATED APPLICATIONS

The present application is a continuation of International Application No. PCT/IL98/00136, filed on Mar. 26, 1998.

FIELD OF THE INVENTION

This invention relates to novel apparatus for effecting on-line measurements of the concentration of active halogens in aqueous and non-aqueous solutions, more particularly to such an apparatus of the potentiostatic type.

BACKGROUND OF THE INVENTION

On-line measurement of the concentration of active halogens in aqueous and non-aqueous solutions is of great importance for many industrial and civil operations, such as halogenation reactions, bromine and chlorine production and disinfection of water or sewages by hypochlorites or hypobromites.

In principle, determination of active halogens may be accomplished by one of the following methods:

a. Titrimmetric analysis

Samples of the analyzed solution are reacted with a reducing reagent, generally sodium thiosulphate. The equivalent point is detected either by a change of color or by an abrupt change in the potential of a platinum electrode. The titration can be carried out either manually or by commercial automatic titrators. However, this is not an on-line method and even when performed automatically not more than 6–10 determinations per hour can be accomplished.

b. Potentiometry

The potential of a platinum electrode is measured in comparison to a reference electrode. This potential, according to the Nernst equation, depends on the concentrations of both the active halogen and the halide. Therefore, unless the halide concentration is essentially constant, this method is essentially qualitative. Daily calibration is required in order to compensate for drifts in the potential of the reference electrode.

c. Photometry

This method is applicable when dealing with clear solutions that contain a single colored active halogen ($I_2$, $Br_2$) and provided that other constituents of the solution do not absorb in the same wavelength range as the active halogen. Even then, this method is restricted to a narrow range of concentrations, as the practical measuring range of absorbance is 0.2–1.5. The necessary instrumentation is delicate and expensive.

d. Voltammetry

Voltammetry includes a variety of electrochemical methods in which the current-potential dependence is measured. Under proper conditions, which include constant hydrodynamic conditions and sufficiently large overpotential, diffusion controlled current that is proportional to the concentration of the electroactive species and is independent of potential, may be attained. This principle is implemented in various electroanalytical methods such as polarography and RDE (Rotating Disc Electrode). Voltammetry, therefore, may provide a straightforward means for the measurement of active halogen concentrations.

Constant hydrodynamic conditions in a voltammetric cell can be sustained either by forced flow of the solution or by a constant movement of the electrode (rotation or vibration).

Voltammetric cells may be of the 2 or 3-electrode type. In the cells of the second type, current flows between two electrodes, called working and counter (auxiliary) electrode (hereinafter designated sometimes by the abbreviations WE and CE respectively), while a preset potential difference between the working electrode and a third electrode, called reference electrode (RE), is maintained. For this mode of operation a special power-supply, called potentiostat, is needed. Potentiostats are discussed e.g. in Allen J. Bard, Larry R Faulkner, "Electrochemical Methods-Fundamentals and Applications", John Wiley & Sons, 1980, p. 563.

The last three methods (b, c, d) can be applied in an "on-line" mode, however only in voltammetry the directly measured signal (current) is proportional to the concentration.

Industrial plants frequently use two-wire transmitters for monitoring various parameters such as temperature, conductance, etc., at points along the production line. The information from the transmitters is fed into a computer which may control the process. The checking points are some time located at long distances from the control station, with no access to the mains. The wires supply the energy required for the transmitter (16 to 40 Volts, 4 mA minimal current) and, at the same time feed back the information by changing the current flowing through the wires. Thus the transmitter is, virtually a current generator adjusted to the range of 4 to 20 mA for the minimal and maximal signals expected, respectively, regardless of the potential applied (from 18 to 40 volts, an error of 0.1% in the current reading is allowed). The transmitter is also unaffected by line noise excluding noise generated by the transducer proper.

Such transmitters are, in general, cheap electronic devices, manufactured by many companies. They require, however, a transducer and some electronic interfacing circuitry. Many companies offer various types of transmitters, which include the transducer and the current generator, all enclosed in one case. The most popular units available are the temperature, pH and conductivity transmitters. None of them, however, is adapted to potentiostatic systems.

SUMMARY OF THE INVENTION

The invention provides a potentiostatic analyzer for active halogens in conducting (aqueous or non-aqueous) solutions that contain also the halide (for example bromine in bromide solution),which is characterized in that it comprises, in combination:

a concentration-to-current transducer, which is an electrolytic cell; means for providing a controlled flow of the solution being analyzed through the cell; and a potentiostatic transmitter proper for controlling the electrodes of the electrolytic cell.

Means for transmitting the information generated by the cell to means for elaborating it are present in potentiostatic analyzers of the art and therefore also in the analyzers of the invention, and need not be described.

The cell comprises a body, through which the sample solution flows, and three electrodes: Working electrode (WE), Counter electrode (CE) and Reference electrode (RE).

The means for providing a controlled flow of the solution through the cell comprise a conduit for the sample solution, having two terminals between which the cell is inserted, and means for maintaining in said conduit a constant head—viz. a constant difference of level—constituting the hydrostatic pressure, or hydrostatic head, for the flow of the solution.

The potentiostatic transmitter comprises a constant current generator, a voltage stabilizing device, a potentiostat connected to said voltage stabilizing device, a follower connected to said potentiostat and a power source. The current produced by the follower is added to that produced by the constant current generator. The potentiostatic analyzer of the invention also comprises a concentration-to-current transducer, which is the electrolytic cell, and which is connected to said potentiostat.

DETAILED DESCRIPTION OF PREFERRED EMBODIMENTS

Figure 1:
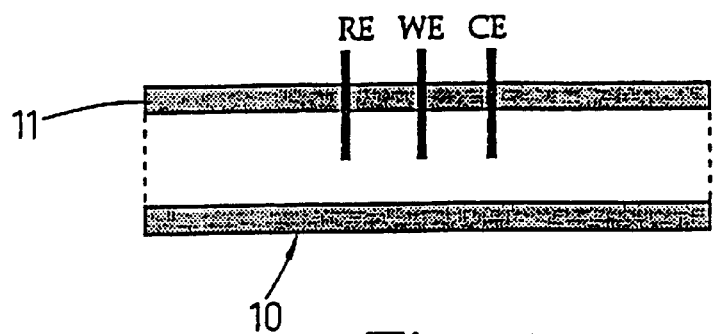
FIG. 1 is a schematic axial cross-section of a electrode cell according to an embodiment of the invention.

FIG. 1 schematically illustrates, in schematic axial cross-section, the electrode cell, generally indicated at 10, which is part of the apparatus of the invention, according to an embodiment thereof. The cell is made of a glass tube 11 into which 3 Pt wires, 0.7 mm in diameter and 7 mm long, are installed, these measures being, of course, mere examples. The Pt wires serve as working, counter and reference electrodes (WE, CE, & RE). The cell is clamped between flanges 12 and 13 shown in FIG. 2.

Figure 2:
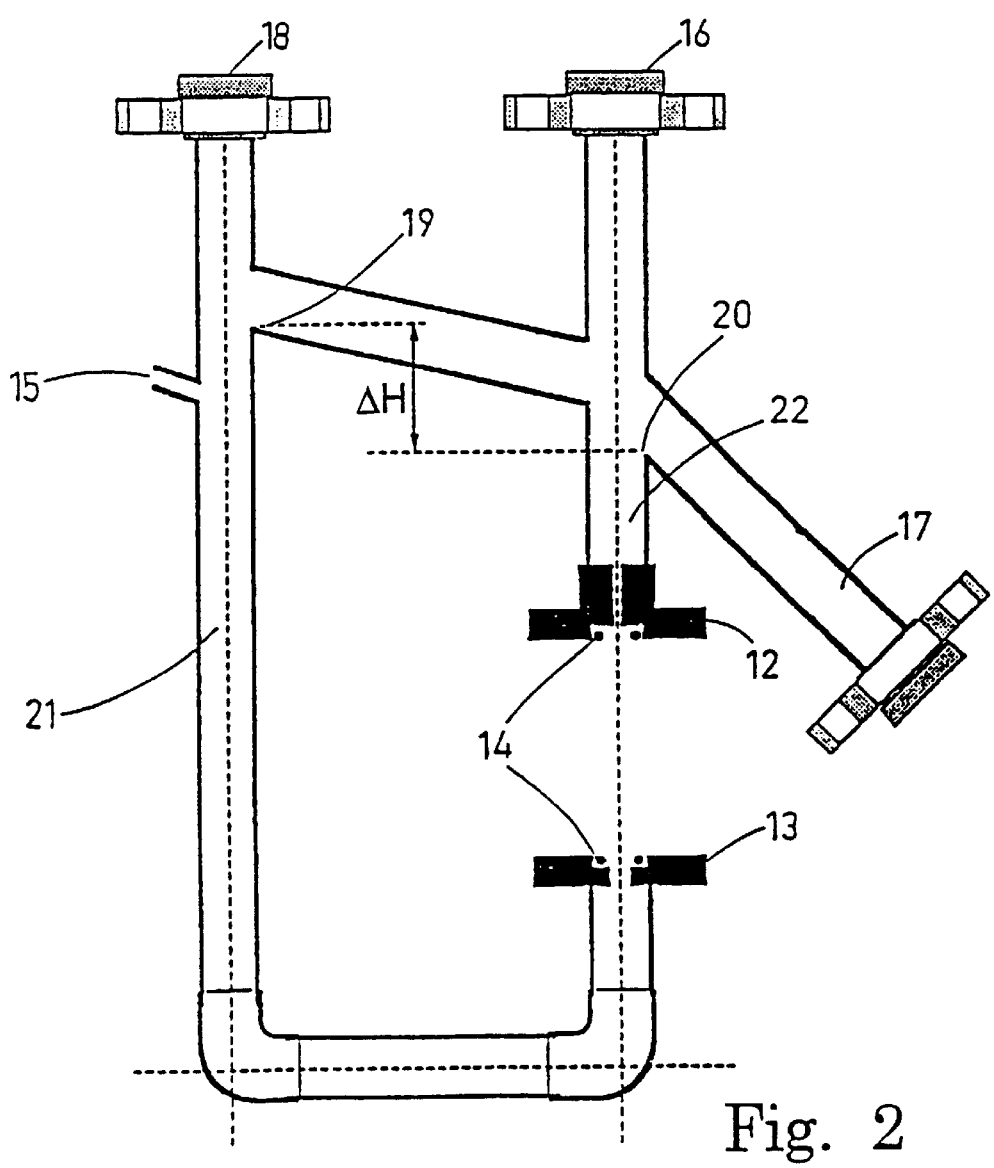
FIG. 2 is a schematic vertical cross-section of the constant head flow conduit according to an embodiment of the invention, in which the cell of FIG. 1 is inserted.

FIG. 2 illustrates the constant head flow system in schematic vertical cross-section. The function of said system is to maintain constant flow rate of the analyzed solution through the cell. Preferably, the system is constructed mainly of polyvinylidene fluoride (PVDF), e.g. Kynar® or Foraflon®, and operates as follows:

The solution to be analyzed flows into the system through inlet 18. The two overflows 19 and 20 ensure that solution level in the left vertical tube 21 is higher then in the right one 22. The electrode cell is clamped, as has been said, between flanges 12 and 13. Gaskets 14 ensure its effective sealing. The constant height difference ("constant hydrostatic head") ΔH maintains constant flow rate through the electrode cell. Most of the resistance to the flow of solution is exerted by the orifice in the upper flange 12.

Auxiliary solutions may be added through the inlet 15. A temperature probe can be inserted into the solution through flange 16. Tube 17 provides an outlet for the analyzed solution.

Figure 3:
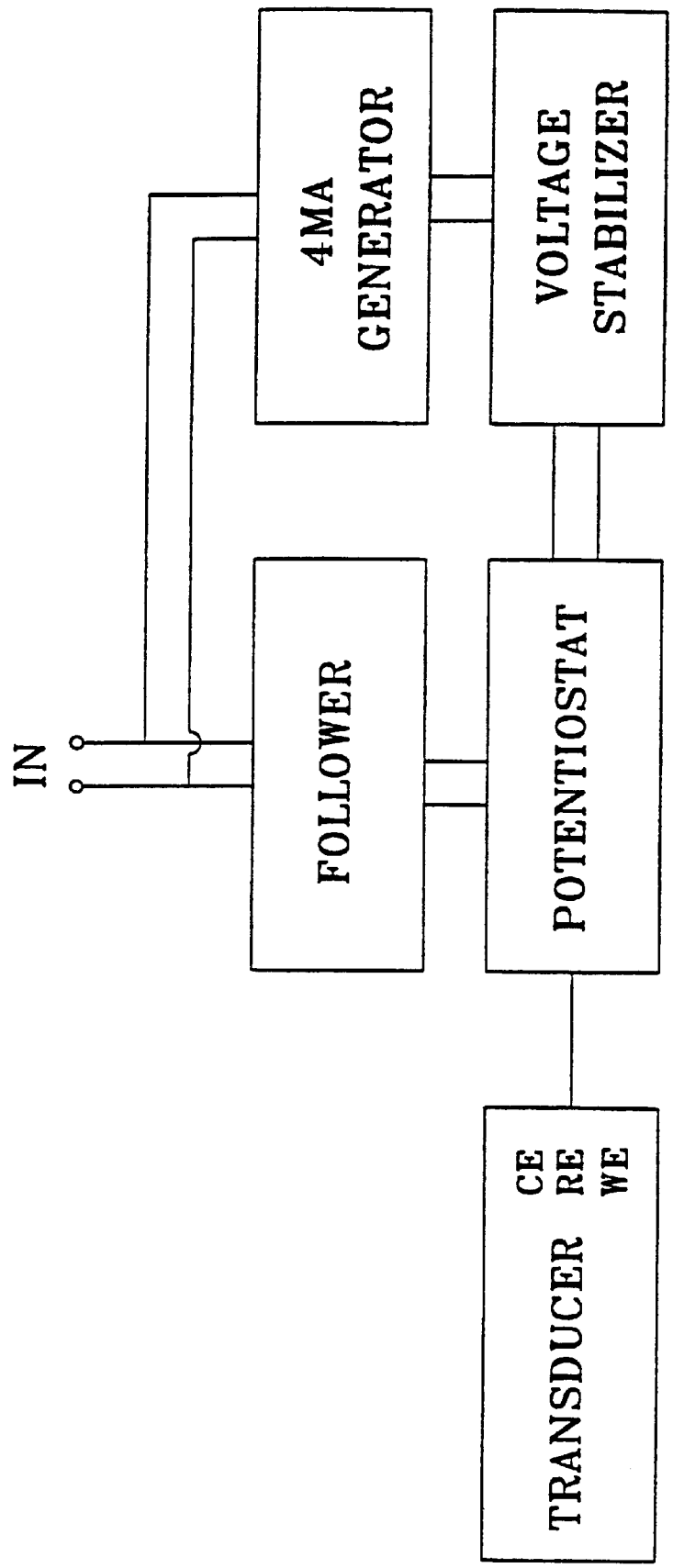
FIG. 3 is a block diagram generally illustrating the invention.

FIG. 3 is a block diagram illustrating how a potentiostatic transmitter, being part of an embodiment of the invention, is functionally combined with other components for effecting on-line analysis. According to the regular values of voltage and current used in the transmitter (24 V and 10 mA respectively), the total energy is of the order of 1/4 W. Special low power circuitry is therefore used. The device contains a constant current generator that is adjusted to 4.00 mA. This current generates a constant potential across a voltage stabilizing device (zener diode). The potentiostat is connected in parallel to the diode and to the power source.

The current generated by the transducer flows through a follower connected directly to the power source and the transducer. When a zero signal is applied, the follower output is zero and the total current of the device is 4.00 mA; when the maximal signal is applied to the transmitter, the follower output is 16 mA and the total current is 20 mA.

Figure 4:
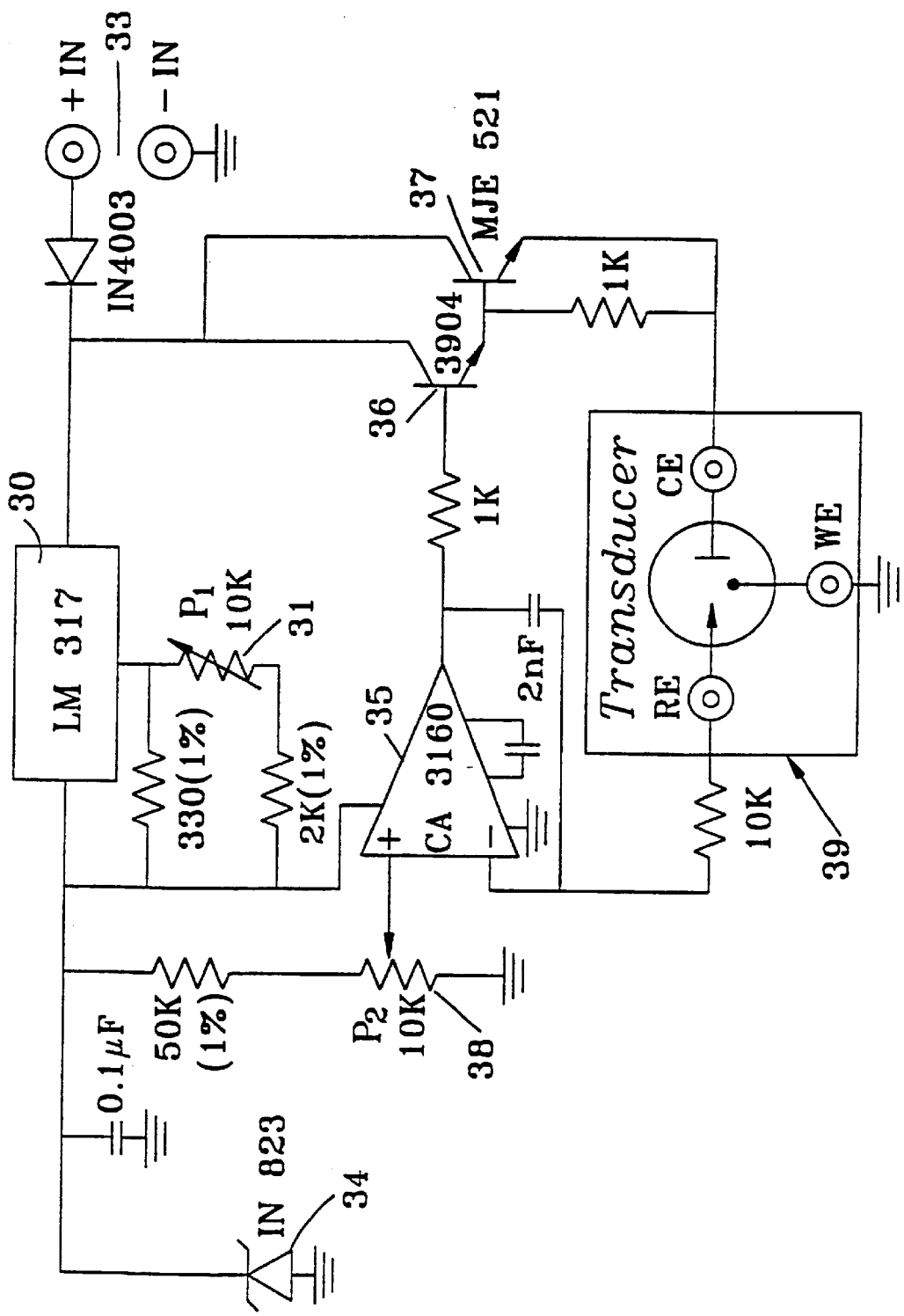
FIG. 4 is a circuit diagram of an apparatus according to an embodiment of the invention.

The design of the potentiostatic transmitter, as shown in FIG. 4, is based on discrete components. The current generator is an accurate voltage regulator (LM 317) indicated at 30, trimmed to 4.00 mA by the load connected to the sense and output leads (variable resistor P1, indicated at 31). A reference diode (IN 823), indicated at 34, connected to the current source is the voltage stabilizer and maintains a potential of 6 Volts approximately. The operational amplifier (CA 3160) 35 is used as a potentiostat, which drives two transistors 36, 37, connected in a Darlington configuration and which form the follower. Numeral 39 generally indicates the concentration-to-current transducer, viz. the three-electrode electrolytic cell. The collectors of the transistors are connected to the positive input of the power source 33, and the current flowing through the cell, supplied by the transistor emitters, is added to the 4.00 mA of the current generator. Obviously this is also the current that flows through the working electrode. The potential of the reference electrode (vs. the working electrode, viz. the ground) is equal to the potential applied by means of a second variable resistor (P2) indicated at 38.

The invented analyzer is distinguished in its simplicity, its minimal maintenance needs and its low price, as it will be shown in the following detailed description of the operation of its three main parts.

The electrochemical cell takes advantage of the simultaneous presence in the analyzed solution of the oxidized and the reduced forms of the redox couple (for example: $Br_2$ & $Br$). Thus the RE, through which practically no current flows, will stay at the reversible potential of the redox couple and may serve as a quasi-reference electrode which is practically maintenance-free. This eliminates the need for the common $Hg/Hg_2Cl_2$ or $Ag/AgCl$ electrodes which must be serviced periodically.

Furthermore, the potential that is applied on the WE (vs. the reversible potential of the couple) is actually the overpotential, so even when the ratio of oxidized to reduced forms alters, and consequently the reversible potential is changed, the WE will continue to operate at the same overpotential. This of course is not true in the case of $Hg/Hg_2Cl_2$ or $Ag/AgCl$ reference electrodes.

The Constant Head Flow System, as explained before, permits to maintain constant hydrodynamic conditions in the electrode cell. The alternatives are to use a dosing pump or a moving working electrode such as a RDE. In both cases it implies dealing with electrical motors that require connection to mains and need regular servicing. Use of a RDE will obviously require also construction of a suitable flow cell that will provide adequate insulation of the corrodable parts of the RDE from the halogen vapors.

The alternative to the potentiostatic transmitter is the use of a commercial potentiostat whose price (>$1000) is higher by more than an order of magnitude. This, of course, will still need interphasing with the computer through a transmitter, and connection of the potentiostat to the mains.

While an embodiment of the invention has been described by way of illustration, it will be apparent that the invention may be carried into practice with many modifications, variations and adaptations, without departing from its spirit or exceeding the scope of the claims.

What is claimed is:

1. A potentiostatic analyzer for active halogens in a conducting solution comprising a corresponding halide, said analyzer comprising:

a concentration-to-current transducer comprising an electrolytic cell;

a hydrostatic head providing a controlled flow of said solution through said cell; and a potentiostatic transmitter for controlling the electrodes of said cell.

2. The analyzer of claim 1 wherein said cell comprises a body through which said solution flows, a working electrode, a counter electrode and a reference electrode, said reference electrode comprised of platinum.

3. The analyzer of claim 1 further comprising a conduit, said conduit comprising two terminals between which said cell is inserted, and wherein said hydrostatic head comprises two overflows disposed on said conduit such that said solution is maintained at a constant difference of level.

4. The analyzer of claim 1 wherein said potentiostatic transmitter comprises a constant generator, a voltage stabilizing device, a potentiostat connected to said voltage stabilizing device, a follower connected to said potentiostat, and a power source, and wherein the electrolytic cell is connected to said potentiostat.

5. The analyzer of claim 4 wherein said constant current generator is adjusted to 4.00 mA.

6. The analyzer of claim 5 wherein the current produced by said constant current generator generates a constant potential across said voltage stabilizing device.

7. The analyzer of claim 4 wherein said follower comprises two transistors connected in Darlington configuration.

8. A potentiostatic analyzer for active halogens in a conducting solution comprising a corresponding halide, said analyzer comprising:

a first tube having an upper end, a lower end, and a solution inlet at said upper end;

a second tube having an upper end and a lower end;

an electrolytic cell comprising electrodes extending into said second vertical tube between said upper end and said lower end;

a potentiostatic transmitter connected to and controlling said electrodes;

a third tube having an upper end and a lower end, said upper end of said third tube connected to and in communication with said first tube at a point between said upper end and said lower end of said first tube, said lower end of said third tube connected to and in communication with said second tube at a point between said upper end of said second tube and said electrodes, and said upper end of said third tube disposed above said lower end of said third tube; and a fourth tube having an upper end and a lower end, said upper end of said fourth tube connected to and in communication with said second tube at a point between said lower end of said third tube and said electrodes, said lower end comprising an outlet and disposed below said upper end of said fourth tube.

9. The analyzer of claim 8 wherein the lower end of said first tube is in communication with said lower end of said second tune.

* * * * *

UNITED STATES PATENT AND TRADEMARK OFFICE
CERTIFICATE OF CORRECTION

PATENT NO. : 6,241,864 B1
DATED : June 5, 2001
INVENTOR(S) : Bejerano et al.

Page 1 of 1

It is certified that error appears in the above-identified patent and that said Letters Patent is hereby corrected as shown below:

Column 2,
Line 19, "some time" should read -- sometimes --.
Line 24, "is, virtually" should read -- is virtually --.

Column 3,
Line 10, "a" should read -- an --.

Column 6,
Line 27, "tune." should read -- tube. --

Signed and Sealed this

Eleventh Day of December, 2001

Attest:

NICHOLAS P. GODICI
Attesting Officer
Acting Director of the United States Patent and Trademark Office